United States Patent [19]

Freed et al.

[11] 4,446,323
[45] May 1, 1984

[54] TETRA- AND HEXA-HYDROPYRROLO(1,2-A)QUINOXA- LINE AND AZAQUINOXALINE DERIVATIVES

[75] Inventors: Meier E. Freed, Paoli, Pa.; Magid Abou-Gharbia, Wilmington, Del.

[73] Assignee: American Home Products Corporation, New York, N.Y.

[21] Appl. No.: 496,791

[22] Filed: May 23, 1983

[51] Int. Cl.³ ............... C07D 471/14; C07D 487/04; A61K 31/495
[52] U.S. Cl. .................... 544/344; 544/346; 546/281; 548/532; 424/250
[58] Field of Search ............... 544/346, 344

[56] References Cited

U.S. PATENT DOCUMENTS 4,089,958 5/1978 Freed et al. .................... 424/250
4,138,564 2/1979 Freed et al. .................... 544/346
4,151,280 4/1979 Rowlands et al. .................... 424/250

FOREIGN PATENT DOCUMENTS 1054955 2/1967 France .

OTHER PUBLICATIONS

Artico et al., Chem. Abstracts 68 105157p (1968).
Derwent report 58761 C/34 (80).
Derwent report 16737 X/09 (76).

Adegoke et al., J. Het. Chem. 19 1169 (1982).

*Primary Examiner*—Mark L. Berch
*Assistant Examiner*—Chabi C. Kalita
*Attorney, Agent, or Firm*—Richard K. Jackson

[57] ABSTRACT

Tetra- and hexa-hydropyrrolo[1,2-a]quinoxaline and azaquinoxaline derivatives of the formula:

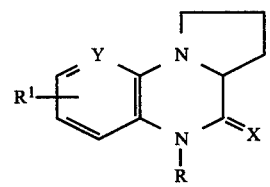

in which
X is O or $H_2$;
Y is CH or N;
R is hydrogen, alkyl, dialkylaminoalkyl, arylalkyl, phenoxyalkyl, benzoyl, pyridylalkyl or variations thereof; and
$R^1$ is hydrogen, alkyl, alkoxy, nitro, halo, trifluoromethyl, amino, alkylamino or dialkylamino;
or pharmaceutically acceptable salts thereof; are antihypertensive agents.

15 Claims, No Drawings

TETRA- AND HEXA-HYDROPYRROLO(1,2-A)QUINOXALINE AND AZAQUINOXALINE DERIVATIVES

DESCRIPTION OF THE INVENTION

This invention provides a group of anti-hypertensive agents of the formula:

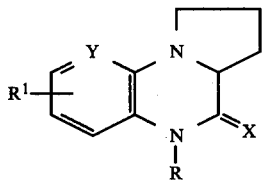

in which
X is O or $H_2$;
Y is CH or N;
R is hydrogen, alkyl of 1 to 6 carbon atoms, dialkylaminoalkyl in which each alkyl group contains 1 to 6 carbon atoms, arylalkyl of 7 to 16 carbon atoms, phenoxyalkyl of 7 to 12 carbon atoms, benzoyl, 4-pyridylalkyl of 6 to 11 carbon atoms, substituted phenylalkyl, substituted benzoyj or substituted phenoxyalkyl wherein the substitution on said phenylalkyl, benzoyl or phenoxyalkyl moieties is by 1, 2 or 3 substituents independently selected from alkyl, alkoxy, nitro, halo, trifluoromethyl, amino, alkylamino and dialkylamino substituents wherein each of said alkyl or alkoxy groups in said substituents contains from 1 to 6 carbon atoms;
with the proviso that when R is hydrogen, Y is N; and
$R^1$ is hydrogen, alkyl of 1 to 6 carbon atoms, alkoxy of 1 to 6 carbon atoms, nitro, halo, trifluoromethyl, amino, alkylamino of 1 to 6 carbon atoms or dialkylamino in which each alkyl group contains from 1 to 6 carbon atoms;
or a pharmaceutically acceptable salt thereof.

The alkyl and alkoxy substituents are preferably fairly small, such as methyl, ethyl, propyl, isopropyl, butyl, tertiary butyl and the corresponding oxy substituents. The halo substituent may be chloro, bromo, fluoro or iodo. The pharmaceutically acceptable salts include salts of both inorganic and organic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic.

The compounds of this invention are prepared by condensing

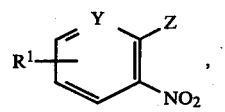

in which Z is chlorine, bromine or fluorine with pyrrolidine-2-carboxylic acid to obtain

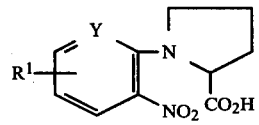

Reduction of the nitro group is accomplished conventionally with a reducing agent such as powdered iron in glacial acetic acid or with sodium dithionite at a pH of about 8-10. Where necessary, by adjusting the pH of the resulting solution containing the carboxy-amine to below 7.5 (preferably to a pH of about 2 to 3) the ring closed amide is produced. The resulting carbonyl group may be reduced with conventional agents such as lithium aluminum hydride.

The antihypertensive activity of the compounds of this invention was established by standard tests in spontaneously hypertensive rats. Thus, a group of at least 4 rats is given the compound by the oral (P.O.) route. Systolic blood pressure, as measured by an indirect technique using the Decker Caudal Plethysmorgraph, is measured prior to administration of the compound and at 1.5, 4 and 24 hours thereafter. This schedule may vary depending upon the behavior of the compound. A control group of rats, given either a placebo or a standard antihypertensive agent is run with each group of treated rats.

When administered in doses of 50 to 150 mg/kg., the compounds of the invention demonstrate slight to marked abilities to reduce blood pressure. When employed to lower blood pressure, the effective dosage of the substance active for such treatment will vary according to the particular compound being employed and the severity and nature of condition being treated. Therapy should be initiated at lower doses (ca. 50 mg/kg.) and thereafter increased, if necessary, to produce the desired anti-hypertensive or anti-secretory effect.

Several compounds of this invention have exhibited $Ca^{+2}$ antagonism in rabbit aortic strips contracted in an organ bath containing Krebs physiological salt solution, following the procedure of Broekaert et al., Eur. J. Pharmacol. 53 281-288 (1979), at a $10^{-5}$ molar bath concentration of the active compound. For example, the product of Example 11 produced 30% inhibition at $10^{-5}$ M, while the product of Example 3 afforded 54% inhibition at $10^{-5}$ M.

Further, when employed as anti-hypertensive agents, the compounds of the invention, or pharmacologically acceptable acid addition salts thereof, may be administered alone or in combination with pharmaceutically acceptable carriers. The proportion and nature of such carriers would be determined by the solubility and other chemical properties of the compound selected, the chosen route of administration, and standard pharmaceutical practice.

The following examples further illustrate the best mode of practicing this invention.

EXAMPLE 1

6a, 7,8,9-Tetrahydropyrido[3,2-e]pyrrolo[1,2-a]pyrazin-6(5H)-one

A solution of 49.94 g. (0.315 mole) of 2-chloro-3-nitropyridine, 36.38 g. (0.316 mole) of L(-)proline and 60 ml. of triethylamine in 450 ml. of dimethylsulfoxide was heated at 60° C. with stirring for 18 hours.

The mixture was diluted with 1.5 l. of cold water, extracted with diethyl ether and the aqueous layer was acidified to pH 3 with concentrated hydrochloric acid and extracted repeatedly with methylene chloride. The combined methylene chloride extracts were dried (Na$_2$SO$_4$) and concentrated. The residue was crystallized from ethyl acetate/pentane to give 65 g. (87% yield) of N-(3-nitro-2-pyridinyl)pyrrolidine-2-carboxylic acid, m.p. 137°–139° C.

Analysis for: $C_{10}H_{11}N_3O_4$; Calculated: C, 50.63; H, 4.64; N, 17.72; Found: C, 50.82; H, 4.80; N, 17.52.

Method A

N-(3-nitro-2-pyridinyl)pyrrolidine-2 carboxylic acid (26 g., 0.1 mole) was dissolved in 800 ml. of water and the pH was adjusted to 9–10 using 50% sodium hydroxide solution. To this stirred solution was added in small portions 70 g. of sodium dithionite. The pH was monitored during the addition and was readjusted to pH 9. The reaction mixture was stirred for one hour and then cooled and acidified with concentrated hydrochloric acid to a pH of 2. The separated solid which was filtered, washed with water and dried, was crystallized from ethanol-diethyl ether (1:1) to give 6.2 g. (30% yield) of the title compound, m.p. 182°–184° C. The hydrochloride salt was prepared by dissolving the free base in ethanol and then treating the solution with diethyl ether saturated with hydrogen chloride gas. The separated solid was recrystallized from ethanol to give white crystals, m.p. 268°–270° C.

Analysis for: $C_{10}H_{11}N_3O$ HCl ½H$_2$O; Calculated: C, 53.01; H, 5.30; N, 18.41; Found: C, 52.79; H, 5.42; N, 18.31.

Method B

To a stirred solution of N-(3-nitro-2-pyridinyl)pyrrolidine-2-carboxylic acid (26 g., 0.1 mole) in 250 ml. of glacial acetic acid was added 12 g. of iron powder over a period of one hour. The temperature of the reaction was raised to 80° C. and it was allowed to stir between 60°–65° C. for three hours. The reaction mixture was cooled and filtered, and the acetic acid was evaporated under reduced pressure. The remaining slurry was extracted with three 300 ml. portions of methylene chloride. The methylene chloride extracts were pooled, dried (Na$_2$SO$_4$) and removed under reduced pressure. The residue was crystallized from ethanol-diethyl ether (1:1) to give 11 g. (59% yield) of the title compound, m.p. 182°–184° C.

EXAMPLE 2

5-[(2,6-dimethoxyphenyl)methyl]-6a,7,8,9-tetrahydropyrido[3,2-e]pyrrolo[1,2-a]pyrazin-6(5H)-one To a stirred solution of 6a,7,8,9-tetrahydropyrido[3,2-e]pyrrolo[1,2-a]pyrazin-6(5H)-one (2.7 g. 0.01 mole) in 30 ml. of dry dimethyl formamide was added sodium hydride (0.5 g., 0.02 mole of 50% dispersion in mineral oil). When the evolution of hydrogen subsides, 2.7 g. (0.01 mole) of 2,6-dimethoxybenzyl chloride was added. The reaction mixture was stirred at room temperature for eighteen hours, and the dimethyl formamide was removed under vacuo. The residue was triturated with cold water, filtered and recrystallized from ethanol to give white crystals of the title compound, 2.7 g. (89% yield) m.p. 200°–202° C.; hydrochloride salt, m.p. 220°–223° C.

Analysis for: $C_{19}H_{21}N_3O_3$ HCl; Calculated: C, 60.71; H, 5.85; N, 11.18; Cl, 9.45; Found: C, 61.16; H, 5.96; N, 11.25; Cl, 9.40.

EXAMPLE 3

5-[(2,6-dimethoxyphenyl)methyl]-5,6,6a,7,8,9-hexahydropyrido[3,2-e]pyrrolo[1,2-a]pyrazine Lithium aluminum hydride (1 g.) was dissolved in 100 ml. of anhydrous diethyl ether. To the stirred solution was added over a period of fifteen minutes a solution of 6a,7,8,9-tetrahydro-5-[(2,6-dimethoxyphenyl)methyl]-pyrido[3,2-e]pyrrolo[1,2-a]pyrazin-6(5H)-one (1 g., 0.003 mole) in 50 ml. of dry tetrahydrofuran. The reaction mixture was refluxed for eighteen hours and was worked up by adding wet ether, filtering, drying and evaporating in vacuo. The residue (m.p. 110°–112° C.) was dissolved in ethanol and treated with diethyl ether saturated with hydrogen chloride. The separated solid was recrystallized from methanol to afford 0.7 g. (67% yield) of the title compound as the hydrochloride salt, m.p. 211°–213° C.

Analysis for: $C_{19}H_{22}N_3O_2$ HCl ½H$_2$O; Calculated: C, 61.53; H, 6.74; N, 11.33; Cl, 9.58; Found: C, 61.67; H, 6.74; N, 11.30; Cl, 9.35.

EXAMPLE 4

5,6,6a,7,8,9-hexahydropyrido[3,2-e]pyrrolo[1,2-a]pyrazine

Following the procedure of Example 3, 6a,7,8,9-tetrahydropyrido[3,2-e]pyrrolo[1,2-a]pyrazin-6(5H)-one is reduced with lithium aluminum hydride to afford the title compound as the hydrochloride salt, m.p. 198°–201° C.

Analysis for: $C_{10}H_{13}N_3$ HCl; Calculated: C, 56.73; H, 6.61; N, 19.65; Cl, 16.78; Found: C, 56.57; H, 6.87; N, 19.73; Cl, 16.63.

EXAMPLE 5

6a,7,8,9-tetrahydro-5-(phenylmethyl)pyrido[3,2-e]-pyrrolo[1,2-a]pyrazin-6(5H)-one The title compound was produced following the procedure of Example 2 with the exception that benzyl chloride was employed rather than 2,6-dimethoxybenzyl chloride; m.p. 222°–225° C., as the hydrochloride, ¼ hydrate.

Analysis for: $C_{17}H_{18}ClN_3O$ ¼H$_2$O; Calculated: C, 63.75; H, 5.78; N, 13.12; Found: C, 63.62; H, 5.72; N, 13.20.

EXAMPLE 6

6a,7,8,9-tetrahydro-5-(4-pyridinylmethyl)pyrido[3,2-e]pyrrolo[1,2-a]pyrazin-6(5H)-one The title compound as produced following the procedure of Example 2 with the exception that 4-pyridyl methyl chloride was employed rather than 2,6-dimethoxybenzyl chloride; m.p. 262°–265° C., as the dihydrochloride, monohydrate.

Analysis for: $C_{16}H_{16}N_4O$ 2HCl H$_2$O; Calculated: C, 51.75; H, 5.40; N, 15.09; Cl 19.13; Found: C, 51.38; H, 5.83; N, 15.08; Cl, 19.17.

EXAMPLE 7

5-[3-(2,3-dimethylphenoxy)-2-hydroxypropyl]-6a,7,8,9-tetrahydropyrido[3,2-e]pyrrolo[1,2-a]pyrazine-6-one To a stirred solution of the product of Example 1 (2.7 g., 0.015 mole) in 40 ml. of dry DMF was added 0.6 g. of sodium hydride (0.025 mole of 50% dispersion in mineral oil). After the evolution of gases subsided, 2.6 g. (0.015 mole) of 1,2-epoxy-3-[2,3-dimethylphenoxy]propane was added. The reaction mixture was stirred overnight and DMF was evaporated in vacuo and the residue was extracted with 200 ml. of diethyl ether. The ether layer was dried and concentrated in vacuo to 30 ml. TLC indicated the presence of two products, one of which is a major component (about 80%). The ether layer was cooled overnight and the separated solid was filtered and recrystallized from diethyl ether to afford 1.8 g. (51% yield) of the title compound m.p. 123°–125° C.

Analysis for: $C_{12}H_{25}N_3O_3$; Calculated: C, 68.66; H, 6.81; N, 11.44; Found: C, 68.93; H, 6.88; N, 11.39.

EXAMPLE 8

5-[2-(dimethylamino)ethyl]-6a,7,8,9-tetrahydropyrido[3,2-e]pyrrolo[1,2-a]pyrazin-6(5H)-one The title compound is produced following the procedure of Example 2 with the exception that dimethylaminoethyl chloride was employed rather than 2,6-dimethoxybenzyl chloride; m.p. 248°–251° C., as the dihydrochloride, monohydrate.

Analysis for: $C_{14}H_{22}Cl_2N_4O$ $H_2O$; Calculated: C, 47.66; H, 6.83; N, 15.95; Cl, 20.22; Found: C, 47.68; H, 6.34; N, 15.86; Cl, 19.98.

EXAMPLE 9

5-(2,6-dimethoxybenzoyl)-1,2,3,3a,4,5-hexahydropyrrolo[1,2-a]quinoxaline

To a stirred solution of the 1,2,3,3a,4,5-hexahydropyrrolo[1,2-a]quinoxaline 1.7 g. (0.009 mole) and 4 ml. of dry triethylamine in 50 ml. of dry acetone was added 2.5 g. (0.01 mole) of 2,6-dimethoxybenzoyl chloride. The reaction mixture was stirred for three hours and filtered, and the acetone was evaporated under vacuo. The residue was washed with water, dried and recrystallized from aqueous ethanol to afford 2.4 g. (79% yield) of the title compound, m.p. 140°–142° C.

Analysis for: $C_{20}H_{22}N_2O_3$; Calculated: C, 71.00; H, 6.50; N, 8.28; Found: C, 70.67; H, 6.48; N, 7.60.

EXAMPLE 10

1,2,3,3a-tetrahydro-5-(phenylmethyl)pyrrolo[1,2-a]quinoxalin-4(5H)-one

Following the procedure of Example 2, 1,2,3,3a-tetrahydropyrrolo[1,2-a]quinoxalin-4(5H)-one is reacted with benzyl chloride to afford the title compound, m.p. 156°–157° C.

Analysis: for: $C_{18}H_{18}N_2O$; Calculated: C, 77.69; H, 6.47; N, 10.07; Found: C, 77.79; H, 6.45; N, 10.27.

EXAMPLE 11

5-[(2,6-dimethoxyphenyl)methyl]-1,2,3,3a-tetrahydropyrrolo[1,2-a]quinoxalin-4(5H)-one Following the procedure of Example 10, with the exception that 2,5-dimethoxybenzyl chloride was employed rather than benzyl chloride, the title compound was produced, m.p. 128°–130° C.

Analysis for: $C_{20}H_{22}N_2O_3$; Calculated: C, 71.00; H, 6.50; N, 8.20; Found: C, 70.49; H, 6.43; N, 8.22.

EXAMPLE 12

1,2,3,3a,4,5-hexahydro-5-[(2,6-dimethoxyphenyl)methyl]pyrrolo[1,2-a]quinoxaline

Following the procedure of Example 3 the product of Example 11 is reduced to afford the title product, m.p. 124°–125° C.

Analysis for: $C_{20}H_{24}N_2O_2$ $\frac{1}{2}H_2O$; Calculated: C, 72.07; H, 7.50; N, 8.40; Found: C, 72.34; H, 7.33; N, 8.44.

EXAMPLE 13

1,2,3,3a-tetrahydro-5-(4-pyridinylmethyl)pyrrolo[1,2-a]quinoxalin-4(5H)-one

Following the procedure of Example 10, with the exception that 4-pyridylmethyl chloride is employed rather than benzyl chloride, the title compound is produced, m.p. 185°–187° C.

Analysis for: $C_{17}H_{17}N_3O$; Calculated: C, 73.11; H, 6.09; N, 15.05; Found: C, 73.30; H, 6.25; N, 15.11.

EXAMPLE 14

5-[2-(dimethylamino)ethyl]-1,2,3,3a-tetrahydropyrrolo[1,2-a]quinoxalin-4(5H)-one Following the procedure of Example 10, with the exception that dimethylaminoethyl chloride is employed rather than benzyl chloride, the title compound is produced as dihydrochloride hydrate, m.p. 150°–153° C.

Analysis for: $C_{15}H_{21}N_3O$ $2HCl$ $H_2O$; Calculated: C, 51.42; H, 6.85; N, 12.00; Cl, 20.28; Found: C, 51.58; H, 6.81; N, 11.59; Cl, 20.22.

What is claimed is:

1. A compound of the formula:

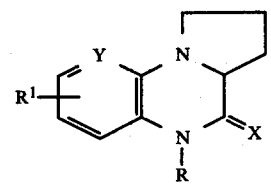

in which

X is O or $H_2$;

Y is CH or N;

R is hydrogen, alkyl of 1 to 6 carbon atoms, dialkylaminoalkyl in which each alkyl group contains 1 to 6 carbon atoms, arylalkyl of 7 to 16 carbon atoms, phenoxyalkyl of 7 to 12 carbon atoms, benzoyl, 4-pyridylalkyl of 6 to 11 carbon atoms, substituted phenylalkyl, substituted benzoyl or substituted phenoxyalkyl wherein the substitution on said phenylalkyl, benzoyl or phenoxyalkyl moieties is by 1, 2 or 3 substituents independently selected from alkyl, alkoxy, nitro, halo, trifluoromethyl, amino, alkylamino and dialkylamino substituents wherein each of said alkyl or alkoxy groups in said substituents contains from 1 to 6 carbon atoms;

with the proviso that when R is hydrogen, Y is N; and $R^1$ is hydrogen, alkyl of 1 to 6 carbon atoms, alkoxy of 1 to 6 carbon atoms, nitro, halo, trifluoromethyl, amino, alkylamino of 1 to 6 carbon atoms or dialkylamino in which each alkyl group contains from 1 to 6 carbon atoms;
or a pharmaceutically acceptable salt thereof.

2. A compound of claim 1 which is 6a,7,8,9-tetrahydropyrido[3,2-e]pyrrolo[1,2-a]pyrazin-6(5H)-one.

3. A compound of claim 1 which is 5-[(2,6-dimethoxyphenyl)methyl]-6a,7,8,9-tetrahydropyrido-[3,2-e]pyrrolo[1,2-a]pyrazin-6(5H)-one.

4. A compound of claim 1 which is 5-[(2,6-dimethoxyphenyl)methyl]-5,6,6a,7,8,9-hexahydropyrido-[3,2-e]pyrrolo[1,2-a]pyrazine.

5. A compound of claim 1 which is 5,6,6a,7,8,9-hexahydropyrido[3,2-e]pyrrolo[1,2-a]pyrazine.

6. A compound of claim 1 which is 6a,7,8,9-tetrahydro-5-(phenylmethyl)pyrido[3,2-e]-pyrrolo[1,2-a]pyrazin-6(5H)-one.

7. A compound of claim 1 which is 6a,7,8,9-tetrahydro-5-(4-pyridinylmethyl)pyrido[3,2-e]-pyrrolo[1,2-a]pyrazin-6(5H)-one.

8. A compound of claim 1 which is 5-[3-(2,3-dimethylphenoxy)-2-hydroxypropyl]-6a,7,8,9-tetrahydropyrido[3,2-e]pyrrolo[1,2-a]pyrazine-6-one.

9. A compound of claim 1 which is 5-[2-(dimethylamino)ethyl]-6a,7,8,9-tetrahydropyrido-[3,2-e]pyrrolo[1,2-a]pyrazin-6(5H)-one.

10. A compound of claim 1 which is 5-(2,6-dimethoxybenzoyl)-1,2,3,3a,4,5-hexahydropyrrolo-[1,2-a]quinoxaline.

11. A compound of claim 1 which is 1,2,3,3a-tetrahydro-5-(phenylmethyl)pyrrolo[1,2-a]-quinoxalin-4(5H)-one.

12. A compound of claim 1 which is 5-[(2,6-dimethoxyphenyl)methyl]-1,2,3,3a-tetrahydropyrrolo-[1,2-a]quinoxalin-4(5H)-one.

13. A compound of claim 1 which is 1,2,3,3a,4,5-hexahydro-5-[(2,6-dimethoxyphenyl)methyl]-pyrrolo[1,2-a]quinoxaline.

14. A compound of claim 1 which is 1,2,3,3a-tetrahydro-5-(4-pyridinylmethyl)pyrrolo-[1,2-a]quinoxalin-4(5H)-one.

15. A compound of claim 1 which is 5-[2-(dimethylamino)ethyl]-1,2,3,3a-tetrahydropyrrolo-[1,2-a]quinoxalin-4(5H)-one.

* * * * *